US012797642B2

(12) United States Patent
Chang et al.

(10) Patent No.: US 12,797,642 B2
(45) Date of Patent: Nov. 17, 2026

(54) SYSTEMS AND METHODS FOR DETERMINING A LOCATION OF A GROSS TARGET VOLUME OF A PATIENT

(71) Applicant: SIEMENS HEALTHINEERS INTERNATIONAL AG, Steinhausen (CH)

(72) Inventors: Yao-Jen Chang, Princeton, NJ (US); Brian Da Silva Teixeira, Princeton, NJ (US); Ankur Kapoor, Plainsboro, NJ (US); Simon Arberet, Princeton, NJ (US); Anand Santhanam, Monmouth Junction, NJ (US); Florin-Cristian Ghesu, Baiersdorf (DE); Ali Kamen, Skillman, NJ (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 84 days.

(21) Appl. No.: 19/003,134

(22) Filed: Dec. 27, 2024

(65) Prior Publication Data

US 2026/0183572 A1 Jul. 2, 2026

(51) Int. Cl.

*A61N 5/10* (2006.01)
*G06T 7/00* (2017.01)
*G06T 7/20* (2017.01)

(52) U.S. Cl.

CPC ......... *A61N 5/1067* (2013.01); *A61N 5/1037* (2013.01); *A61N 5/1077* (2013.01);
(Continued)

(58) Field of Classification Search

CPC .. A61N 5/1067; A61N 5/1037; A61N 5/1077; A61N 2005/1074; G06T 7/0012; G06T 7/20; G06T 2207/10116; G06T 2207/20081; G06T 2207/20084; G06T 2207/30096

See application file for complete search history.

(56) References Cited

U.S. PATENT DOCUMENTS

2010/0172469 A1* 7/2010 Poulsen .................. A61B 6/12
378/65
2026/0175048 A1 6/2026 Chang et al.

OTHER PUBLICATIONS

Cho et al., "A monoscopic method for real-time tumour tracking using combined occasional x-ray imaging and continuous respiratory monitoring" Physics in Medicine and Biology, vol. 53, 2008, pp. 2837-2855.

(Continued)

*Primary Examiner* — Kiho Kim
(74) *Attorney, Agent, or Firm* — Foley & Lardner LLP

(57) ABSTRACT

Provided herein are systems for predicting a location of a gross target volume in a patient. In examples, systems include one or more processors that are configured to obtain image data associated with a plurality of two-dimensional (2D) images. The one or more processors can be configured to determine a location of one or more lesions at the first point in time and determine a future location of the one or more lesions at a second point in time based on the location of the one or more lesions and a trajectory representing expected motion of the one or more lesions. In examples, the one or more processors can be configured to generate a control signal to cause a linear accelerator to move based on the future location of the one or more lesions.

20 Claims, 8 Drawing Sheets

(52) U.S. Cl.
CPC .............. *G06T 7/0012* (2013.01); *G06T 7/20* (2013.01); *A61N 2005/1074* (2013.01); *G06T 2207/10116* (2013.01); *G06T 2207/20081* (2013.01); *G06T 2207/20084* (2013.01); *G06T 2207/30096* (2013.01)

(56) References Cited

OTHER PUBLICATIONS

Choi et al., "Real-Time Tumor Motion Tracking in 3D Using Planning 4D CT Images during Image-Guided Radiation Therapy" Algorithms, vol. 11, 2018, 155 (14 pages).
Ernst et al., "Predicting the outcome of respiratory motion prediction" Medical Physics, vol. 28, Issue 10, Oct. 2011 (Abstract only, 6 pages).
Finn et al., "Model-Agnostic Meta-Learning for Fast Adaptation of Deep Networks", Proceedings of the 34th International Conference on Machine Learning, Sydney, Australia, PMLR 70, 2017 (13 pages).
Kilby et al., "The CyberKnife(R) Robotic Radiosurgery System in 2010" Technology in Cancer Research and Treatment, vol. 9, No. 5, Oct. 2010, pp. 433-452.
Park et al., "3D Trajectory Reconstruction under Perspective Projection" International Journal of Computer Vision, vol. 115, Feb. 2015 (Abstract only, 8 pages).
Remmerts de Vries et al., "Markerless 3D tumor tracking during single-fraction free-breathing 10MV flattening-filter-free stereotactic lung radiotherapy" Radiotherapy and Oncology, vol. 164, 2021, pp. 6-12.
Sitzmann et al., "Implicit Neural Representations with Periodic Activation Functions" arXiv, Jun. 2006 (35 pages).
Wiersma et al., "Combined kV and MV imaging for real-time tracking of implanted fiducial markersa)" Medical Physics, vol. 35, Issue 4, Apr. 2008 (Abstract only, 5 pages).
Yoganathan et al., "Magnitude, Impact, and Management of Respiration-induced Target Motion in Radiotherapy Treatment: A Comprehensive Review" Journal of Medical Physics, vol. 42, Issue 3, Jul. 2017, pp. 101-115.

* cited by examiner

500

SYSTEMS AND METHODS FOR DETERMINING A LOCATION OF A GROSS TARGET VOLUME OF A PATIENT

TECHNICAL FIELD

This application relates generally to systems and methods for predicting a location of a gross target volume in a patient during radiotherapy treatment and, in some embodiments, to systems and methods for predicting a location of a gross target volume in a patient during radiotherapy treatment by modeling motion of one or more lesions of the gross target volume over time.

BACKGROUND

Radiotherapy (also referred to as "radiotherapy" or "RT") involves the delivery of radiation (energy) to targets within the body of a patient during treatment. For example, a linear accelerator (LINAC) can be configured to move relative to a patient in accordance with an RT treatment plan to multiple control points and deliver energy to target tissue (e.g., tumors, lesions, etc.) to treat cancer located within the body of the patient. This can allow for the targeted delivery of energy toward the target tissue, with the goal of reducing or eliminating the target tissue without affecting the surrounding tissue.

But conventional methods for implementing treatment plans to treat a patient can be difficult to execute in a controlled manner. For example, anatomical structures, tumor lesions, etc., of a patient can move when breathing, as a result of reflexive movement, and/or as a result of visceral movement (natural movement of organs in the body). This can cause a gross target volume (GTV) targeted during RT treatment to move and be misaligned relative to the LINAC. To reduce the chances of this occurring, patients treated can be instructed to hold their breath (often referred to as a deep inspiration breath-hold or "DIBH") as energy is delivered. But the success of this technique is highly variable and cannot account completely for unintentional or visceral movement. And other techniques that involve monitoring the patient's movement based on external features (e.g., surrogates) can be subject to "drift," resulting in incorrect determinations of the location of the GTV. As a result, the energy delivered to the GTV of the patient may be sub-optimal as some of the energy intended to target the GTV can likewise be misaligned and delivered to different portions of the GTV or one or more organs at risk (OARs).

SUMMARY

For the aforementioned reasons, there is a need for systems and methods that allow for predicting a location of a gross target volume in a patient during radiotherapy treatment by modeling motion of one or more lesions of the gross target volume over time.

The methods and systems discussed herein address the challenge of predicting lesion positions within a 3D space during radiotherapy treatment that, at least in part, can change as a result of unintentional, reflexive, or visceral movement of the patient. More specifically, the presently-disclosed techniques are directed to the modeling of motion of a GTV over time during RT treatment so as to minimize deviations between established locations (e.g., poses, etc.) of lesions within the 3D space and actual locations as they change.

In some embodiments, systems including one or more processors can be configured to obtain image data associated with a plurality of two-dimensional (2D) images generated by imaging devices positioned about a patient. These systems can determine a location of one or more lesions of the patient at a first point in time based on the plurality of 2D images. The systems can then determine a future location of the one or more lesions at a later point in time based on the location of the one or more lesions and a trajectory representing expected motion of the one or more lesions. In some examples, the systems can then generate a control signal to control operation of one or more devices. For example, the systems can generate control signals to control operation of a LINAC during RT treatment, where such control signals adjust the position of one or more components of the LINAC. In other examples the systems can generate control signals to generate beam-eye views of the predicted position of the GTV over time.

By implementing some or all of the techniques described herein, multiple technical benefits can be realized. First, the position of one or more lesions in a 3D space can be more accurately determined as compared to traditional methods. This can, in turn, improve treatment by allowing for more precise delivery of energy during the RT treatment process. Additionally, systems that implement the techniques described herein can account for otherwise unpredictable uncertainties due to unintentional movements, reflexive movements, or visceral movements by the patient. These benefits can allow for reduced consumption of computational resources in addition to improved energy to the delivery. For example, systems including processors and memory that would otherwise be dedicated to the determination of the location of the GTV (e.g., based on the relative movement of surrogates, etc.) can be conserved or reserved entirely. Additionally, medical devices such as a LINAC can be configured to operate with less downtime between instances of delivered energy, resulting in faster delivery of energy to the GTV which can improve the effects of the RT treatments (e.g., the targeting of cells of a lesion for destruction). These benefits collectively contribute to more effective and efficient cancer treatment through improved delivery of energy through radiotherapy.

In an embodiment, a system for predicting a location of a gross target volume in a patient during radiotherapy treatment by modeling motion of one or more lesions of the gross target volume over time is disclosed. The system can include one or more processors configured to obtain image data associated with a plurality of two-dimensional (2D) images. The image data is generated by a plurality of imaging devices positioned about a patient at a first point in time. The system can determine a location of one or more lesions at the first point in time based on the plurality of 2D images. The system can determine a future location of the one or more lesions at a second point in time after the first point in time based on the location of the one or more lesions and a trajectory representing expected motion of the one or more lesions within a three-dimensional (3D) space. The system can generate a control signal to cause a linear accelerator (LINAC) to move from a current pose at the first point in time to a future pose at the second point in time to adjust a beam path of the linear accelerator based on the future location of the one or more lesions.

In aspects, the plurality of 2D images can include two or more X-ray images. The one or more processors can be configured to obtain the image data are configured to obtain two or more X-ray images from the plurality of devices. The X-ray images can include a two-dimensional (2D) representation of at least a portion of the patient at the first point in time. In some aspects, the one or more processors can be configured to determine the location of the one or more lesions at the first point in time are configured to determine a pose of the one or more lesions based on the plurality of 2D images. In some aspects, the one or more processors can be further configured to generate the trajectory representing the expected motion of the one or more lesions based on locations of one or more prior lesions at first points in time and future locations of the one or more prior lesions at second points in time. In at least one aspect, the one or more processors configured to generate the trajectory representing the expected motion of the one or more lesions can be configured to provide the location of the one or more lesions at the first point in time to an adapted motion model to cause the adapted motion model to generate an output representing the trajectory.

In some aspects, the one or more processors configured to provide the location of the one or more lesions to the adapted motion model can be configured to provide the location of the one or more lesions at the first point in time to the adapted motion model. The adapted motion model can be configured to predict a set of future locations for the one or more lesions between the first point in time and the second point in time. In at least one aspect, the system can obtain future location data associated with the set of future locations for the one or more lesions. The system can determine the trajectory based on the set of future locations.

In an aspect, the one or more processors can be further configured to determine a beam-eye view (BEV) of the one or more lesions at the second point in time based on a pose of the LINAC at the second point in time and the future location of the one or more lesions.

In another embodiment, a method can include obtaining, by one or more processors, image data associated with a plurality of two-dimensional (2D) images. The image data can be generated by a plurality of imaging devices positioned about a patient at a first point in time. The method can include determining, by the one or more processors, a location of one or more lesions at the first point in time based on the plurality of 2D images. In some aspects, the method can include determining, by the one or more processors, a future location of the one or more lesions at a second point in time after the first point in time based on the location of the one or more lesions and a trajectory representing expected motion of the one or more lesions within a three-dimensional (3D) space. The method can include generating, by the one or more processors, a control signal to cause a linear accelerator (LINAC) to move from a current pose at the first point in time to a future pose at the second point in time to adjust a beam path of the linear accelerator based on the future location of the one or more lesions.

In an aspect, the plurality of 2D images can include two or more X-ray images. Obtaining the image data can include obtaining, by the one or more processors, two or more X-ray images from the plurality of imaging devices. The X-ray images can include two-dimensional (2D) representations of at least a portion of the patient at the first point in time.

In some aspects, determining the location of the one or more lesions at the first point in time can include determining, by the one or more processors, a pose of the one or more lesions based on the plurality of 2D images. The method can further include generating, by the one or more processors, the trajectory representing the expected motion of the one or more lesions based on locations of one or more prior lesions at first points in time and future locations of the one or more prior lesions at second points in time. Generating the trajectory representing the expected motion of the one or more lesions can include providing, by the one or more processors, the location of the one or more lesions at the first point in time to an adapted motion model to cause the adapted motion model to generate an output representing the trajectory. In aspects providing the location of the one or more lesions to the adapted motion model can include providing, by the one or more processors, the location of the one or more lesions at the first point in time to the adapted motion model. The adapted motion model can be configured to predict a set of future locations for the one or more lesions between the first point in time and the second point in time. The method can include obtaining, by the one or more processors, future location data associated with the set of future locations for the one or more lesions. The method includes determining the trajectory based on the set of future locations. In aspects the method can further include determining, by the one or more processors, a beam-eye view (BEV) of the one or more lesions at the second point in time based on a pose of the LINAC at the second point in time and the future location of the one or more lesions.

In yet another embodiment, a non-transitory computer-readable medium can store instructions thereon that, when executed by one or more processors, cause the one or more processors to obtain image data associated with a plurality of two-dimensional (2D) images. The image data can be generated by a plurality of imaging devices positioned about a patient at a first point in time. The instructions can cause the one or more processors to determine a location of one or more lesions at the first point in time based on the plurality of 2D images. The instructions can cause the one or more processors to determine a future location of the one or more lesions at a second point in time after the first point in time based on the location of the one or more lesions and a trajectory representing expected motion of the one or more lesions within a three-dimensional (3D) space. The instructions can cause the one or more processors to generate a control signal to cause a linear accelerator (LINAC) to move from a current pose at the first point in time to a future pose at the second point in time to adjust a beam path of the linear accelerator based on the future location of the one or more lesions.

In an aspect, the plurality of 2D images can include two or more X-ray images. The instructions that cause the one or more processors to obtain the image data can cause the one or more processors to obtain two or more X-ray images from the one or more imaging devices. The X-ray images can include two-dimensional (2D) representations of at least a portion of the patient at the first point in time. In aspects, the instructions that cause the one or more processors to determine the location of the one or more lesions at the first point in time can cause the one or more processors to determine a pose of the one or more lesions based on the plurality of 2D images. In some aspects, the instructions can further cause the one or more processors to generate the trajectory representing the expected motion of the one or more lesions based on locations of one or more prior lesions at first points in time and future locations of the one or more prior lesions at second points in time.

In another aspect, the instructions that cause the one or more processors to generate the trajectory representing the expected motion of the one or more lesions can cause the one or more processors to provide the location of the one or more lesions at the first point in time to an adapted motion model to cause the adapted motion model to generate an output representing the trajectory. The instructions that cause the one or more processors to provide the location of the one or more lesions to the adapted motion model can cause the one or more processors to provide the location of the one or more lesions at the first point in time to the adapted motion model. The adapted motion model can be configured to predict a set of future locations for the one or more lesions between the first point in time and the second point in time. The instructions can be configured to cause the one or more processors to obtain future location data associated with the set of future locations for the one or more lesions. The instructions can cause the one or more processors to determine the trajectory based on the set of future locations.

In an embodiment, a system for predicting a location of a gross target volume in a patient during radiotherapy treatment by modeling motion of one or more lesions of the gross target volume over time is disclosed. The system can include one or more processors configured to: obtain image data associated with a plurality of two-dimensional (2D) images, the image data generated by a plurality of imaging devices positioned about a patient and representing locations of one or more lesions across a first period of time. The one or more processors can be configured to provide the locations of the one or more lesions to a sequential triangulation network to cause the sequential triangulation network to generate an estimated trajectory representing motion of the one or more lesions over the first period of time. In aspects, the one or more processors can be configured to provide the estimated trajectory to a motion prediction network to cause the motion prediction network to generate a predicted trajectory representing expected motion of the one or more lesions within a three-dimensional (3D) space over a second period of time, and determine a future location of the one or more lesions based on a location of the one or more lesions and the predicted trajectory. In some aspects, the one or more processors can be configured to generate a control signal to cause a linear accelerator (LINAC) to move from a first pose to a second pose to adjust a beam path of the linear accelerator based on the future location of the one or more lesions.

In some implementations, the one or more processors can be configured to determine the locations of the one or more lesions across the first period of time based on the plurality of 2D images. The one or more processors to provide the image data to the sequential triangulation network can be configured to provide the image data to the sequential triangulation network, where the sequential triangulation network is trained based on a plurality of four-dimensional computed tomography (CT) scans corresponding to a plurality of previously-observed patients. In aspects, the sequential triangulation network can be trained based on a plurality of estimated 2D images extracted from four-dimensional CT scans generated for the one or more patients.

In some aspects, the one or more processors configured to provide the locations of the one or more lesions to a sequential triangulation network can be configured to condition the sequential triangulation network based on at least a portion of the locations of the one or more lesions. The plurality of 2D images can include two or more X-ray images, and the one or more processors configured to obtain the image data can be configured to obtain two or more X-ray images from the plurality of imaging devices, the two or more X-ray images including two-dimensional (2D) representations of at least a portion of the patient across the first period of time. The location of the one or more lesions across the first period of time can represent poses of the one or more lesions in the 3D space. In some aspects, the one or more processors can be further configured to determine a beam-eye view (BEV) of the one or more lesions based on the future location of the one or more lesions and a pose of the LINAC at a second point in time.

In another embodiment, a method for predicting a location of a gross target volume in a patient during radiotherapy treatment by modeling motion of one or more lesions of the gross target volume over time is disclosed. The method can include obtaining, by one or more processors, image data associated with a plurality of two-dimensional (2D) images, the image data generated by a plurality of imaging devices positioned about a patient and representing locations of one or more lesions across a first period of time. In aspects, the method can include providing, by the one or more processors, the locations of the one or more lesions to a sequential triangulation network to cause the sequential triangulation network to generate an estimated trajectory representing motion of the one or more lesions over the first period of time. In some aspects, the method can include providing, by the one or more processors, the estimated trajectory to a motion prediction network to cause the motion prediction network to generate a predicted trajectory representing expected motion of the one or more lesions within a three-dimensional (3D) space over a second period of time. In aspects, the method can include determining, by the one or more processors, a future location of the one or more lesions based on a location of the one or more lesions and the predicted trajectory. In some aspects, the method can include generating, by the one or more processors, a control signal to cause a linear accelerator (LINAC) to move from a first pose to a second pose to adjust a beam path of the linear accelerator based on the future location of the one or more lesions.

In aspects, the method can further include determining, by the one or more processors, the locations of the one or more lesions across the first period of time based on the plurality of 2D images. Providing the image data to the sequential triangulation network can include providing, by the one or more processors, the image data to the sequential triangulation network, where the sequential triangulation network is trained based on a plurality of four-dimensional computed tomography (CT) scans corresponding to a plurality of previously-observed patients. In some aspects, the sequential triangulation network can be trained based on a plurality of estimated 2D images extracted from four-dimensional CT scans generated for the one or more patients. In at least some aspects, providing the locations of the one or more lesions to the sequential triangulation network can include conditioning, by the one or more processors, the sequential triangulation network based on at least a portion of the locations of the one or more lesions. The plurality of 2D images can include two or more X-ray images, and obtaining the image data can include obtaining, by the one or more processors, two or more X-ray images from the plurality of imaging devices, the two or more X-ray images including two-dimensional (2D) representations of at least a portion of the patient across the first period of time.

In some aspects, the location of the one or more lesions across the first period of time can represent poses of the one or more lesions in the 3D space. In some aspects, the method can further include determining, by the one or more processors, a beam-eye view (BEV) of the one or more lesions based on the future location of the one or more lesions and a pose of the LINAC at a second point in time.

In yet another embodiment, a non-transitory computer-readable medium is disclosed as storing instructions thereon that, when executed by one or more processors, cause the one or more processors to: obtain image data associated with a plurality of two-dimensional (2D) images, the image data generated by a plurality of imaging devices positioned about a patient and representing locations of one or more lesions across a first period of time. The instructions can cause the one or more processors to provide the locations of the one or more lesions to a sequential triangulation network to cause the sequential triangulation network to generate an estimated trajectory representing motion of the one or more lesions over the first period of time. In some aspects, the instructions can cause the one or more processors to provide the estimated trajectory to a motion prediction network to cause the motion prediction network to generate a predicted trajectory representing expected motion of the one or more lesions within a three-dimensional (3D) space over a second period of time, and determine a future location of the one or more lesions based on a location of the one or more lesions and the predicted trajectory. In aspects, the instructions can cause the one or more processors to generate a control signal to cause a linear accelerator (LINAC) to move from a first pose to a second pose to adjust a beam path of the linear accelerator based on the future location of the one or more lesions.

In at least some aspects, the instructions can further cause the one or more processors to determine the locations of the one or more lesions across the first period of time based on the plurality of 2D images. In some aspects, the instructions that cause the one or more processors to provide the image data to the sequential triangulation network can cause the one or more processors to provide the image data to the sequential triangulation network, where the sequential triangulation network is trained based on a plurality of four-dimensional computed tomography (CT) scans corresponding to a plurality of previously-observed patients. In aspects, the sequential triangulation network can be trained based on a plurality of estimated 2D images extracted from four-dimensional CT scans generated for the one or more patients.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
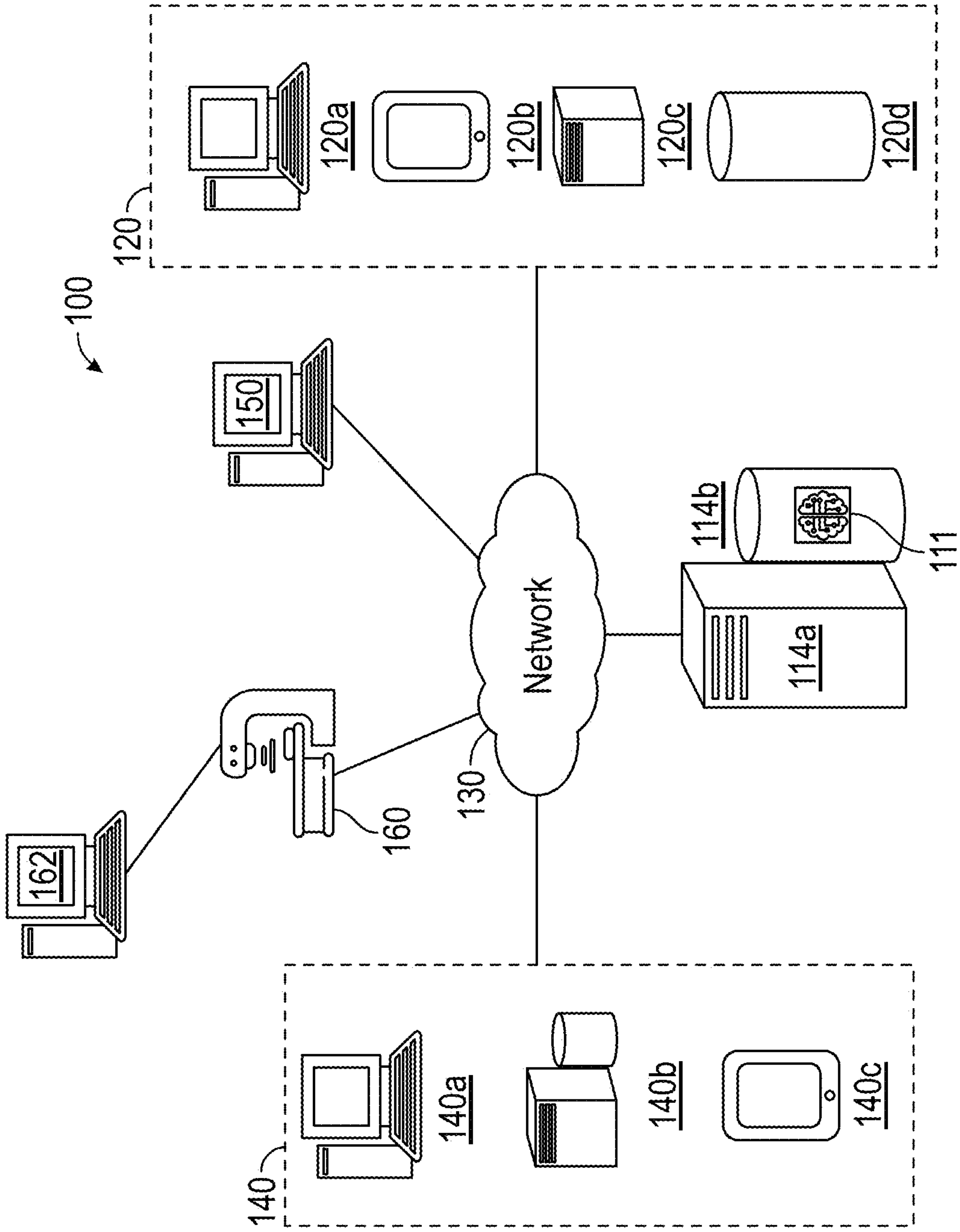
FIG. 1 illustrates a diagram of a system for predicting a location of a gross target volume in a patient during radiotherapy treatment, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are configured to be considered within the scope of the subject matter disclosed herein. Other embodiments can be used, or other changes can be made without departing from the spirit or scope of the present disclosure. The illustrative embodiments described in the detailed description are not meant to be limiting of the subject matter presented.

FIG. 1 illustrates components of a system 100 for predicting a location of a gross target volume in a patient during radiotherapy treatment, according to an embodiment. The system 100 can include an analytics server 114*a*, system database 114*b*, a treatment planning system 111, electronic data sources 120*a-d* (each referred to individually as an electronic data source 120 and collectively electronic data sources 120, unless stated otherwise), end-user devices 140*a-c* (each referred to individually as an end user device 140 and collectively as end-user devices 140, unless stated otherwise), an administrator computing device 150, a medical device 160, and medical device computer(s) 162. Various components depicted in FIG. 1 can belong to a radiotherapy clinic at which patients can receive radiotherapy treatment, in some cases via one or more radiotherapy machines (e.g., medical device 160) located within the clinic. The system 100 is not confined to the components described herein and can include additional or other components, not shown for brevity, which are configured to be considered within the scope of the embodiments described herein.

The above-mentioned components can be connected to each other through a network 130. Examples of the network 130 can include, but are not limited to, private or public local-area-networks (LAN), wireless LAN (WLAN) networks, metropolitan area networks (MAN), wide-area networks (WAN), and the Internet. The network 130 can include wired or wireless communications according to one or more standards or via one or more transport mediums. The communication over the network 130 can be performed in accordance with various communication protocols such as Transmission Control Protocol and Internet Protocol (TCP/IP), User Datagram Protocol (UDP), and IEEE communication protocols. In one example, the network 130 can include wireless communications according to Bluetooth specification sets or another standard or proprietary wireless communication protocol. In another example, the network 130 can also include communications over a cellular network, including, e.g., a GSM (Global System for Mobile Communications), CDMA (Code Division Multiple Access), and EDGE (Enhanced Data for Global Evolution) network.

The analytics server 114*a* can be any computing device comprising a processor and non-transitory machine-readable storage capable of executing the various tasks and processes described herein. The analytics server 114*a* can employ various processors such as central processing units (CPU)

and graphics processing unit (GPU), among others. Non-limiting examples of such computing devices can include workstation computers, laptop computers, server computers, and the like. While the system 100 includes a single analytics server 114*a*, the analytics server 114*a* can include any number of computing devices operating in a distributed computing environment, such as a cloud environment.

The analytics server 114*a* can generate and display an electronic platform configured to use a treatment planning system 111 for receiving patient information and inputs from users (e.g., clinicians) such as utility functions and updated utility functions described herein and outputting the results of execution of the treatment planning system 111. The electronic platform can include graphical user interfaces (GUI) displayed by display devices of one or more electronic data sources 120, the end-user devices 140, the medical device 160, or the administrator computing device 150. An example of the electronic platform generated and hosted by the analytics server 114*a* can be a web-based application or a website configured to be displayed on different electronic devices, such as mobile devices, tablets, personal computers, and the like.

The information displayed by the electronic platform can include, for example, input elements to receive data associated with a patient being treated, synchronize one or more sensors, and display results of predictions produced by the treatment planning system 111. For instance, the analytics server 114*a* can execute the treatment planning system 111 (e.g., a system such as a treatment planner that is configured or trained to generate beam configurations that are usable to configure the medical device 160 when treating a patient, as described herein). The analytics server 114*a* can then display the results for a clinician or directly revise one or more operational attributes of the medical device 160.

The electronic data sources 120 can be any computing device comprising a processor and non-transitory machine-readable storage capable of executing the various tasks and processes described herein. For example, the electronic data sources 120 can represent various computing devices that contain, retrieve, or access data associated with a medical device 160, such as data associated with operational information of currently or previously performed radiotherapy treatments (e.g., electronic log files or electronic configuration files), data associated with current or previously monitored patients (e.g., computed tomography (CT) scans, magnetic resonance imaging (MRI) scans, tumor locations, deformation information, or the like) or participants in a study, or the like. For instance, the analytics server 114*a* can use the clinic computer 120*a*, medical professional device 120*b*, server 120*c* (associated with a clinician or a clinic), and database 120*d* (associated with the clinician or the clinic) to retrieve/receive data associated with the medical device 160. The analytics server 114*a* can retrieve the data from the end-user devices 140, generate a dataset, and use the dataset to configure the treatment planning system 111 (e.g., models implemented by the treatment planning system 111 or the like). The analytics server 114*a* can execute various algorithms to translate raw data received/retrieved from the electronic data sources 120 into machine-readable objects that can be stored and processed by other analytics processes as described herein.

End-user devices 140 can be any computing device comprising a processor and a non-transitory machine-readable storage medium capable of performing the various tasks and processes described herein. Non-limiting examples of an end-user device 140 can be a workstation computer, laptop computer, tablet computer, or server computer. In operation, various users such as clinicians as described herein can use end-user devices 140 to access the GUI operationally managed by the analytics server 114*a* or otherwise the results of the execution of the treatment planning system 111. Specifically, the end-user devices 140 can include clinic computer 140*a*, clinic server 140*b*, and a medical professional device 140*c*. Even though referred to herein as "end-user" devices, these devices cannot always be operated by end-users. For instance, the clinic server 140*b* cannot be directly used by an end user. However, the results stored on the clinic server 140*b* can be used to populate various GUIs accessed by an end user via the medical professional device 140*c*. In some embodiments, the end-user device 140 can be associated with one or more clinicians that are associated with the generation of one or more treatment plans (e.g., involved in preparing the one or more treatment plans) for patients.

The administrator computing device 150 can represent a computing device operated by a system administrator. The administrator computing device 150 can be configured to display radiotherapy treatment attributes generated by the analytics server 114*a* (e.g., various analytics metrics determined during training of one or more machine learning models or systems); monitor various treatment planning systems 111 utilized by the analytics server 114*a*, electronic data sources 120, or end-user devices 140; review feedback; or facilitate training or retraining (calibration) of the treatment planning system 111 that are maintained by the analytics server 114*a*.

In some embodiments, the medical device 160 can be a diagnostic imaging device or a treatment delivery device (also referred to as a radiotherapy system). For example, the medical device 160 can include one or more computed tomography (CT) scanners such as a cone-beam CT (CBCT) scanner, a linear accelerator (LINAC) such as the Varian® TrueBeam® LINAC, proton beam therapy systems (referred to as proton beam systems) that uses accelerated protons to deliver precise radiotherapy to tumors, or other similar devices configured to transmit energy toward targeted tissue (referred to as gross target volumes) associated with a patient and, in some cases, measure the energy transferred to ward the targeted tissue. The medical device 160 can also include one or more sensors configured to monitor the patient being treated. That is, the medical device 160 or the analytics server 114*a* can be communicating with various sensors that can monitor a patient's external biological signals. Non-limiting examples of the sensors can include three-dimensional (3D) surfacing mechanisms, and optical (or other) sensors configured to monitor the patient's movements (e.g., how the patient is moving or breathing. In some embodiments, the medical device 160 can receive data associated with a treatment plan from the medical device computer(s) 162 that cause the medical device 160 to operate in accordance with the treatment plan.

The treatment planning system 111 can be stored in the system database 114*b*. The treatment planning system 111 can be trained using data received/retrieved from the electronic data sources 120 and can be executed using data received from the end-user devices, the medical device 160, or the sensor 163. In some embodiments, the treatment planning system 111 can reside within a data repository local or specific to a clinic. In various embodiments, the treatment planning system 111 can use one or more deep learning engines to develop a treatment plan for a patient using radiotherapy. For instance, the analytics server 114*a* can transmit patient attributes from the sensor 163 and execute the treatment planning system 111 accordingly. The analytics server 114*a* can then display the results on one or more end-user devices 140. In some embodiments, the analytics server **114*a* can change one or more configurations of the medical device 160 based on the results predicted by the treatment planning system 111**.

Figure 2:
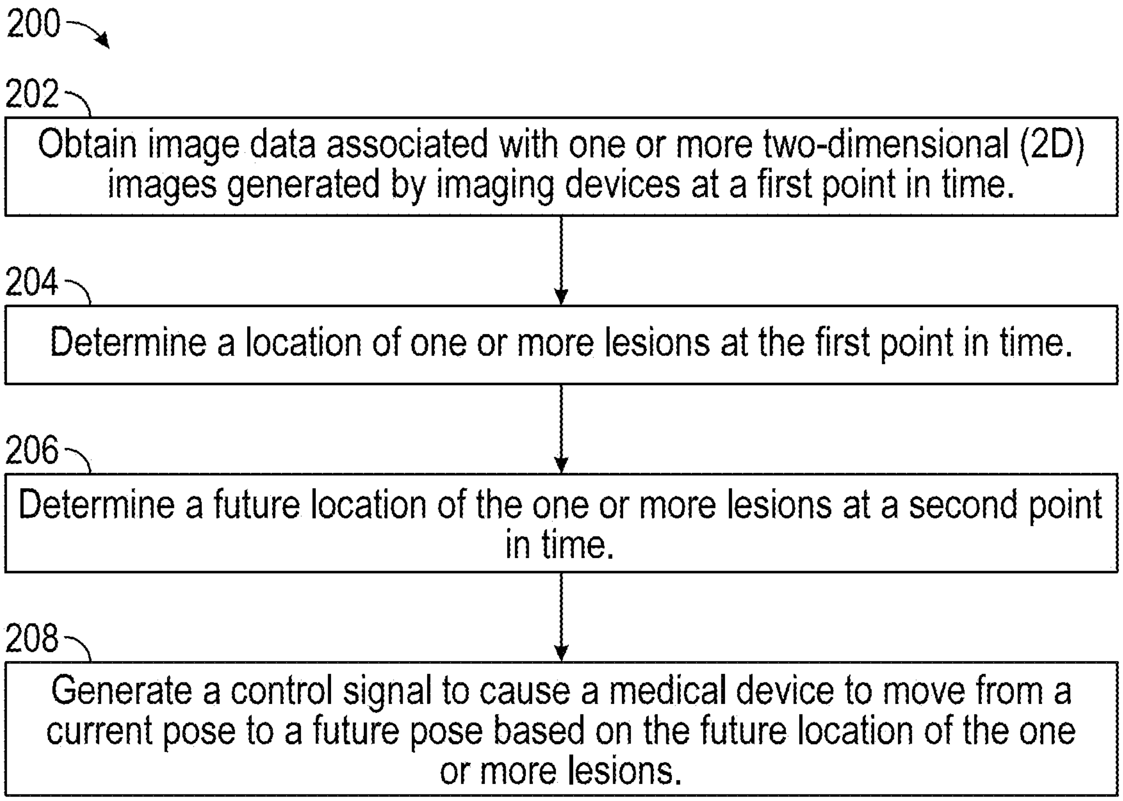
FIG. 2 illustrates a flow diagram of a process for predicting a location of a gross target volume in a patient during radiotherapy treatment, according to an embodiment.

Referring to FIG. 2, illustrated is a flow diagram of a process 200 for predicting a location of a gross target volume in a patient during radiotherapy treatment, according to an embodiment. The process 200 includes operations 202-208. However, other embodiments can include additional or alternative operations or can omit one or more operations altogether. The process 200 is described as being executed by an analytics server, which can be the same as, or similar to, the analytics server **114*a* described in FIG. 1. However, one or more steps of the process 200 can be executed by any number of computing devices operating in the distributed computing system described in FIG. 1. For instance, one or more computing devices can locally perform part, or all of the operations described in FIG. 2**.

At operation 202, the analytics server can obtain image data associated with two or more two-dimensional (2D) images generated by an imaging device. For example, the analytics server can obtain image data associated with two or more 2D images generated by one or more imaging devices positioned about a patient. These imaging devices can include X-ray machines and or the like. In some embodiments, the analytics server can obtain the image data from the plurality of imaging devices, where the plurality of imaging devices is positioned relative to a patient in a 3D space. In this example, the plurality of imaging devices can be positioned relative to the patient along with a medical device (e.g., that is the same as, or similar to, the medical device 160 of FIG. 1) such as a LINAC that is being moved to multiple control points established by a treatment plan to deliver energy to the patient. While the concepts of the present disclosure are discussed with respect to a LINAC, it will be understood that different types of medical devices (e.g., proton beam systems, etc.) are contemplated as being used instead of, or in addition to, the LINAC.

In one example, during RT treatment, a patient can be positioned in relation to a gantry of a LINAC that supports a magnetron or a klystron generating high-energy X-rays for delivery to the lesion of the patient. The LINAC can include a multi-leaf collimator (MLC) that is positioned along a treatment beam path (beam path) that is configured to shape the high energy X-rays as they are directed toward the lesion of the patient. In some embodiments, the plurality of imaging devices can be positioned such that they target at least a portion of the patient including a lesion targeted as part of a treatment plan. For example, during treatment of the patient, the LINAC can be moved to a plurality of control points (e.g., 3D poses within the 3D space that the patient, the LINAC, and the imaging devices are located in) and configured to generate and transmit energy toward the patient at each control point. At each control point, the leaves of the LINAC's MLC can shape the X-rays so as to optimize energy delivery and conformance with the lesion of the patient, while minimizing the delivery of energy outside of the lesion (e.g., to one or more OARs). In some embodiments, a set of control points, MLC leaf configurations, and power levels at which energy is to be delivered can be established by a treatment plan generated prior to the procedure. The analytics server can be configured to perform operations to control the operation of the LINAC as described herein in accordance with a treatment plan developed for that patient.

In some embodiments, the analytics server can obtain the image data at a first point in time. For example, the analytics server can obtain the image data at two or more points in time during a period of time right before the treatment or during a period of time when the patient is being treated during the RT treatment. In this period of time, the imaging devices can be configured to generate images at a plurality of points. In some embodiments, the analytics server can obtain the image data from a plurality of imaging devices, where the image data includes (e.g., represents) two or more X-ray images captured by the one or more imaging devices. The X-ray images can include 2D representations of at least a portion of the patient. For example, the X-ray images captured by the one or more imaging devices can represent corresponding 2D representations of at least a portion of the patient that includes the GTV. As described herein the analytics server can obtain image data at two or more different points in time. To allow for the analytics server to obtain additional image data, the one or more imaging devices can be configured to periodically and or continuously generate the image data and provide the image data to the analytics server.

At operation 204, the analytics server can determine a location of one or more lesions. For example, the analytics server can determine a location of the one or more lesions located in the patient at a first point in time corresponding to the point in time at which the image data was generated. In this example, the analytics server can determine the location of the one or more lesions, where the one or more lesions are located within the GTV of the patient. In some embodiments, the location of the one or more lesions can represent a position and/or orientation (e.g., a pose) of at least a portion of the GTV and be established relative to the one or more imaging devices. The analytics server can then determine a pose of the one or more lesions (e.g., included in the GTV). For example, the analytics server can determine a pose of the one or more lesions in the 3D space where the patient is receiving RT treatment based on the plurality of 2D images captured by the imaging devices positioned relative to the patient.

In some embodiments, the analytics server can determine the location of the one or more lesions based on the analytics server generating one or more trajectories representing expected motion of the one or more lesions using one or more models. For example, the analytics server can generate the one or more trajectories representing the expected motion of the one or more lesions using a model (e.g., a neural network, an adaptive motion model, etc.). In this example, the model can be configured to receive data associated with the position of the one or more lesions at the first point in time and generate an output representing a trajectory. The data associated with the position of the one or more lesions can be represented using a plurality of 2D images captured at the first point in time at which the image data is generated. In some embodiments, analytics server can determine a trajectory based on the output of the model. For example, the analytics server can cause the model to determine (e.g., extract, etc.) the trajectory of the one or more lesions over a period of time starting at the point in time at which the image data was generated. The trajectory can represent motion of the one or more lesions (of at least a portion of the one or more lesions) in 3D space. This motion can be represented as an offset along the X, Y, Z axis. In some examples, this motion can also be represented by changes in velocity over a period of time.

In some embodiments, the analytics server can generate the trajectory using a model that was trained based on locations of one or more prior lesions at first points in time and locations of the one or more prior lesions at future points in time. For example, a training dataset can be established with locations (e.g., poses) of a plurality of lesions at first points in time. In examples, the locations can be determined based on the generation of 2D images similar to as described above of the one or more prior lesions as the one or more prior lesions are tracked by the imaging devices during, for example, earlier performed RT treatments. The training dataset can further include corresponding locations of the one or more prior lesions at second points in time. These locations at the second points in time can be offset by an established period of time from the prior points in time.

The model can then be trained using the training dataset. For example, the analytics server can train the model using the training dataset to output predictions in response to receiving locations of the one or more prior lesions (e.g., established by the two or more 2D images captured during an RT treatment) during RT treatment. In examples, the analytics server can train the model by providing the locations of the one or more prior lesions at the first points in time to the model to cause the model to generate an output. This example, the output can represent a trajectory indicating the predicted motion of the one or more lesions. The analytics server can then compare the output (e.g., the predicted trajectories that, when applied to the location of the GTV, result in repositioning of the GTV to a predicted location) to the location of the one or more prior lesions as initially represented. In some examples, the analytics server can then determine a future location for the one or more prior lesions at second points in time (e.g., based on motion of the on one or more prior lesions from their first location in accordance with the trajectory predicted by the model) and compare the future location to a known future location established by the training dataset. The analytics server can then compare a difference between the predicted location and the known future location, determine a loss based on the difference, and update one or more weights of the model to reduce the loss upon subsequent execution of the model by the analytics server. The analytics server can iteratively repeat this process until the model converges (e.g., the model generates predictions that result in future locations with corresponding losses that satisfy a threshold value responding to an accepted accuracy for the model). This can allow for consistent trajectory prediction of one or more lesions during a subsequently-performed RT treatment by the analytics server.

In some embodiments, once trained, the analytics server can generate the trajectory representing the expected motion of the one or more lesions using the model, where the model is trained on the dataset representing the locations of the one or more prior lesions as they move over time. For example, the analytics server can provide the location of the one or more lesions at the first point in time as an input to the model. In this example, the analytics server can cause the model to execute in accordance with the location of the one or more lesions at the first point in time to generate an output. The output can represent a trajectory indicating the expected motion of the one or more lesions. For example, the output can represent the trajectory of the one or more lesions in 3D space, changes in rate of acceleration over time as the one or more lesions move within the 3D space, and/or the like.

At operation 206, the analytics server can determine a future location of the one or more lesions. For example, the analytics server can determine a future location of the one or more lesions in response to the analytics server generating one or more trajectories representing expected motion of the one or more lesions. As described herein, the analytics server can determine a future location of the one or more lesions within a predetermined period from the point in time at which the image data was generated. For example, the analytics server can determine a future location of the one or more lesions within the 3D space in which the patient is located according to a predetermined time interval after the image data is generated. In this example, the time interval can be associated with (e.g., correspond to) the time during which the one or more lesions move between locations established by the training dataset. In some embodiments, the analytics server and then iteratively repeat one or more of operations 202-206 and predict future locations of the one or more lesions within the 3D space during the course of the RT treatment.

In some embodiments, the analytics server can determine the future location of the one or more lesions based on the location of the one or more lesions at the first point in time and the trajectory generated by the model. For example, the analytics server can determine the future location by applying the trajectory to the points established for the one or more lesions by the image data generated at the first point in time period. In this example, the analytics server can apply transformations to the points representing the one or more lesions in the 3D space in accordance with the trajectory to model the movement of the one or more lesions and predict the future location of the one or more lesions using the model.

At operation 208, the analytics server can generate a control signal to cause a medical device to move from a current position to a future pose. For example, the analytics server can determine a pose of the medical device at the first point in time. At that first point in time, the analytics server can configure the medical device to generate and transmit energy towards the GTV of the patient based on the relative position of the patient compared to the 3D space in which the patient is located and/or the relative position of the medical device. In this example, the analytics server can cause the medical device to generate and transmit the energy in accordance with the treatment plan. For example, the analytics server can be configured to control operation of the medical device in accordance with the treatment plan established prior to the RT treatment of the patient, where the treatment plan indicates one or more control points to move the medical device between, and one or more configurations for the medical device (e.g., one or more power levels to transmit energy at, one or more leaf configurations, etc.). In some embodiments, the analytics server can then predict future locations of the GTV during the course of the RT treatment as described above. For example, the analytics server can predict future locations of the GTV as the medical device is moved from control point to control point and activated to deliver energy to the GTV of the patient. The analytics server can then compare the predicted future locations to the locations established by the treatment plan and control operation of the medical device such that the medical device targets the GTV at the (predicted) future location.

In some embodiments, the analytics server can determine a beam-eye view (BEV). For example, the analytics server can determine a beam-eye view representing a view of the GTV relative to one or more components of the medical device (e.g., a collimator of a LINAC). The beam-eye view can be represented as a 2D representation of the GTV from the point of view of the one or more components of the LINAC. In some embodiments, the beam-eye view can be used by the analytics server when targeting the GTV using the medical device during performance of the RT treatment plan.

Figure 3:
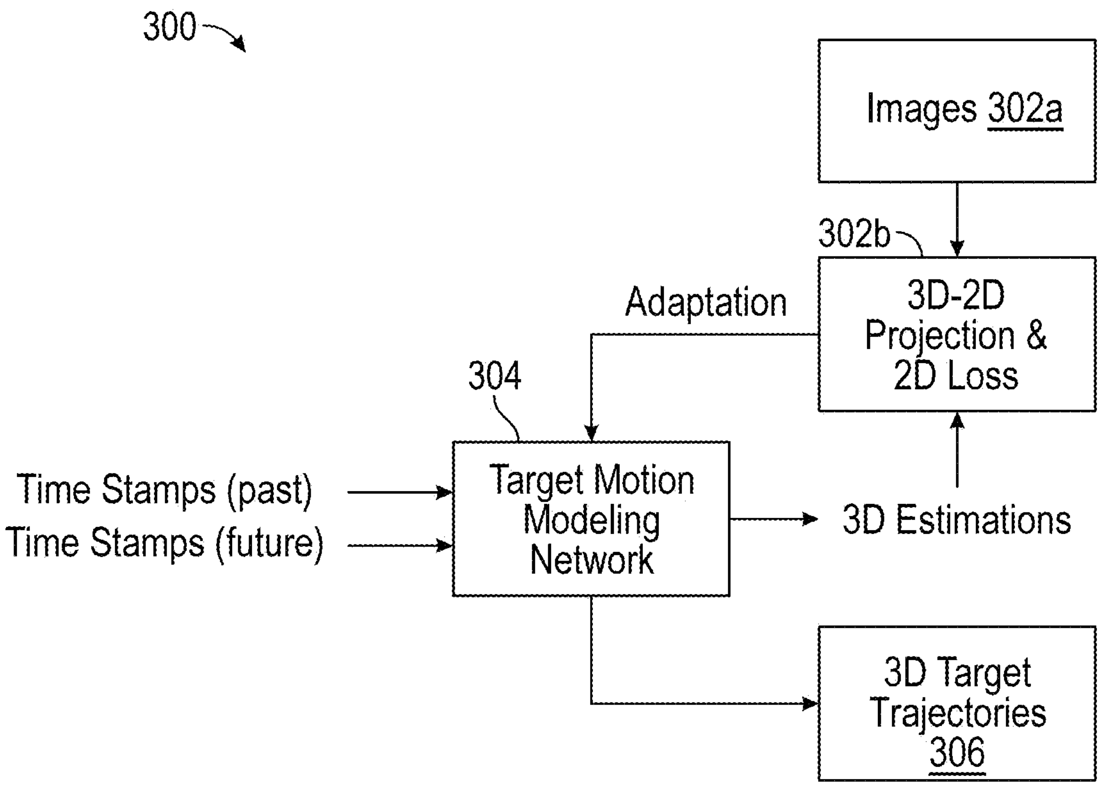
FIG. 3 illustrates an example implementation of a process for predicting a location of a gross target volume in a patient during radiotherapy treatment, according to an embodiment.

Referring to FIG. 3, illustrated is an example implementation 300 of a process for predicting a location of a GTV (including one or more lesions thereof) in a patient during RT treatment, according to an embodiment. As shown in FIG. 3, the implementation 300 involves execution of a target motion modeling network 304. In some examples, the target motion modeling network 304 can be the same as, or similar to, the models described above with respect to FIG. 2 (e.g., the neural network, the adaptive motion model, etc.). In some embodiments, one or more of the operations described with respect to the implementation 300 can be executed by an analytics server that is the same as, or similar to, the analytics server 114*a* of FIG. 1 and/or the analytics server discussed with respect to FIG. 2.

In some embodiments, the implementation 300 can involve one or more operations being executed in accordance with the target motion modeling network 304. For example, the target motion modeling network 304 can be configured to receive one or more past timestamps as input that correspond to images 302*a* captured by a plurality of imaging device positioned about a patient during RT treatment. In this example, the target motion modeling network 304 can be configured to receive a location of the imaging device used to generate the images 302*a*, the location represented as a position/orientation (e.g., pose) of the imaging device in the 3D space where a patient is being treated using a medical device (e.g., a LINAC) as described herein. The target motion modeling network 304 can then perform one or more operations when generating corresponding outputs representing 3D target trajectories 306 (e.g., trajectories as described above with respect to FIG. 2). These 3D target trajectories 306 can correspond to expected motion of one or more lesions (e.g., of a GTV) over a period of time starting at a first point in time (e.g., represented by past time stamps) and a second point in time (e.g., represented by future time stamps). In some embodiments, the 3D target trajectories 306 can be projected onto the 2D X-ray image plane using a projection matrix associated with a plurality of imaging device (e.g., an X-ray image as described herein, a virtual imaging device, etc.) used to generate the images 302*a*. In some embodiments, the projection matrix can be used to project the estimated 3D positions onto the 2D X-ray image plane for comparing against actual 2D observations of the one or more lesions. In response to comparing the estimated 3D positions against the 2D observations, a loss can be computed between predicted locations established by the timestamps at the first point in time and the known locations of the one or more lesions (e.g., at future points in time) established based on the 3D target trajectories 304. During training of the target motion modeling network 304, future timestamps and ground truth observations can be compared to the predicted locations of the one or more lesions to iteratively adjust the parameters of the target motion modeling network 304. This can allow the target motion modeling network 304 to be configured to reconstruct and predict motion of one or more lesions within a GTV within the same implementation 300.

In some embodiments, the target motion modeling network 304 can be configured (e.g., trained) based on meta-learning of an implicit function, where the implicit function is modeled as a deep neural network whose parameters are controlled and learned by another deep neural network. In one embodiment, implicit neural representations can be used with periodic activation functions to model the implicit function. Specifically, the target motion modeling network 304 can use a set of learnable sine functions as periodic activation functions, which are more flexible for modeling semi-periodic lesion motion than a set of predetermined basis vectors. In some embodiments, the meta-learning can involve execution of a Model-Agnostic Meta-Learning (MAML) framework for fast adaptation of model parameters. In examples, the MAML framework can adapt the global model parameters pretrained with many offline population samples so that these parameters can be quickly adapted to a specific sample. In examples described herein, population samples can be used from multiple patients to obtain the global model (e.g., a global target motion modeling network 304), allowing the global model to be quickly fine-tuned from short-term observations of a specific patient to reconstruct the 3D trajectory and predict future target motion.

Figure 4:
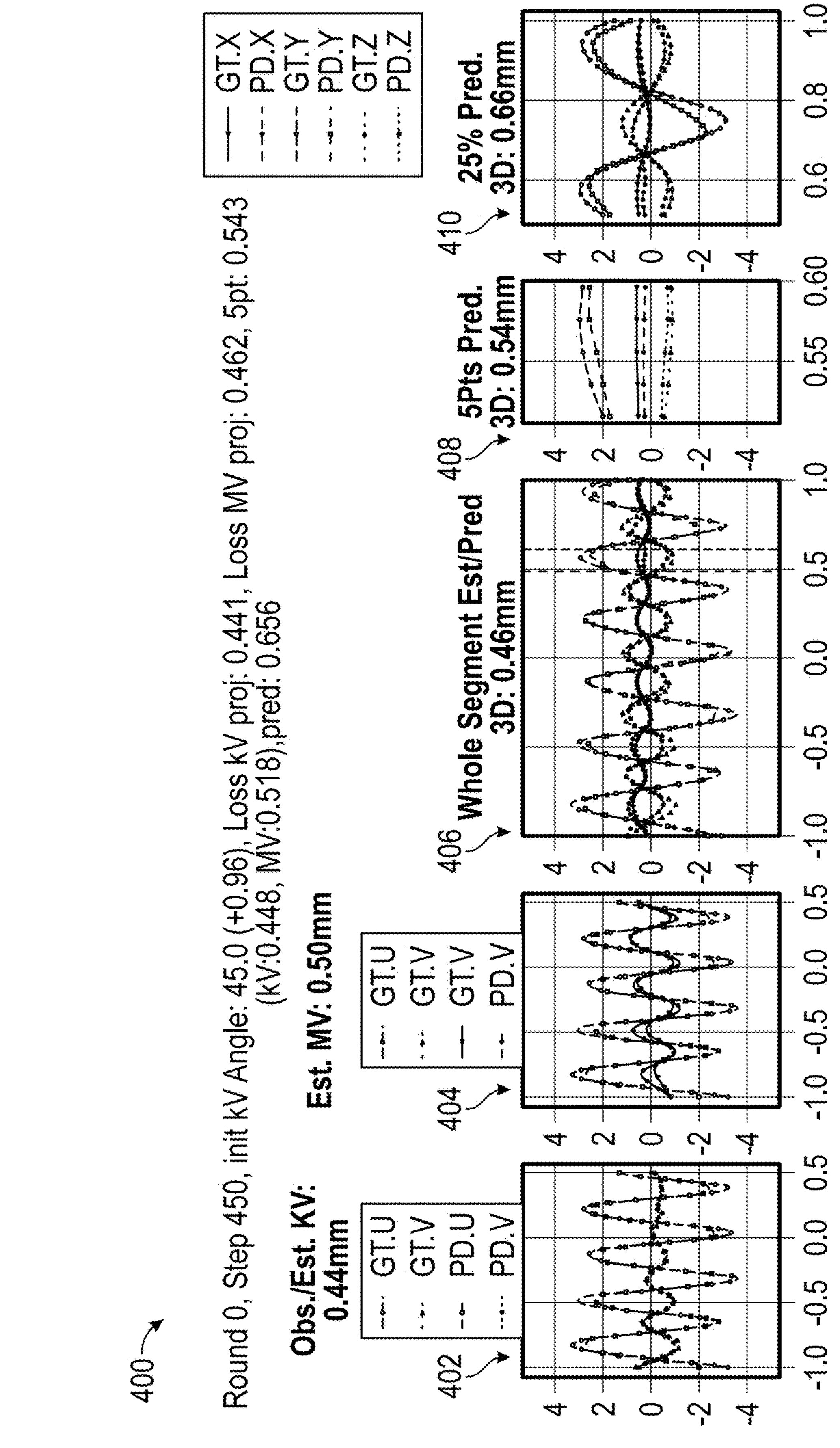
FIG. 4 illustrates an example of target motion modeling that can be established during execution of an implementation, according to an embodiment.

FIG. 4 illustrates an example 400 of target motion modeling that can be established during execution of the implementation 300, according to an embodiment. As illustrated, a ground truth "GT" trajectory and an estimated or predicted "PD" trajectory are illustrated. The first two columns 402, 404 show projected trajectories in the kV (X-ray) and MV (beam) coordinate systems, respectively. The third column 406 shows the 3D trajectory in three axes, with values within the normalized timestamp from −1.0 to 0.5 being reconstructed and values from 0.5 to 1.0 being predicted. The fourth column 408 shows a zoomed-in view of the first five predicted signals, while the fifth column 410 shows a zoomed-in view of all predicted signals within the timestamp from 0.5 to 1.0.

Figure 5:
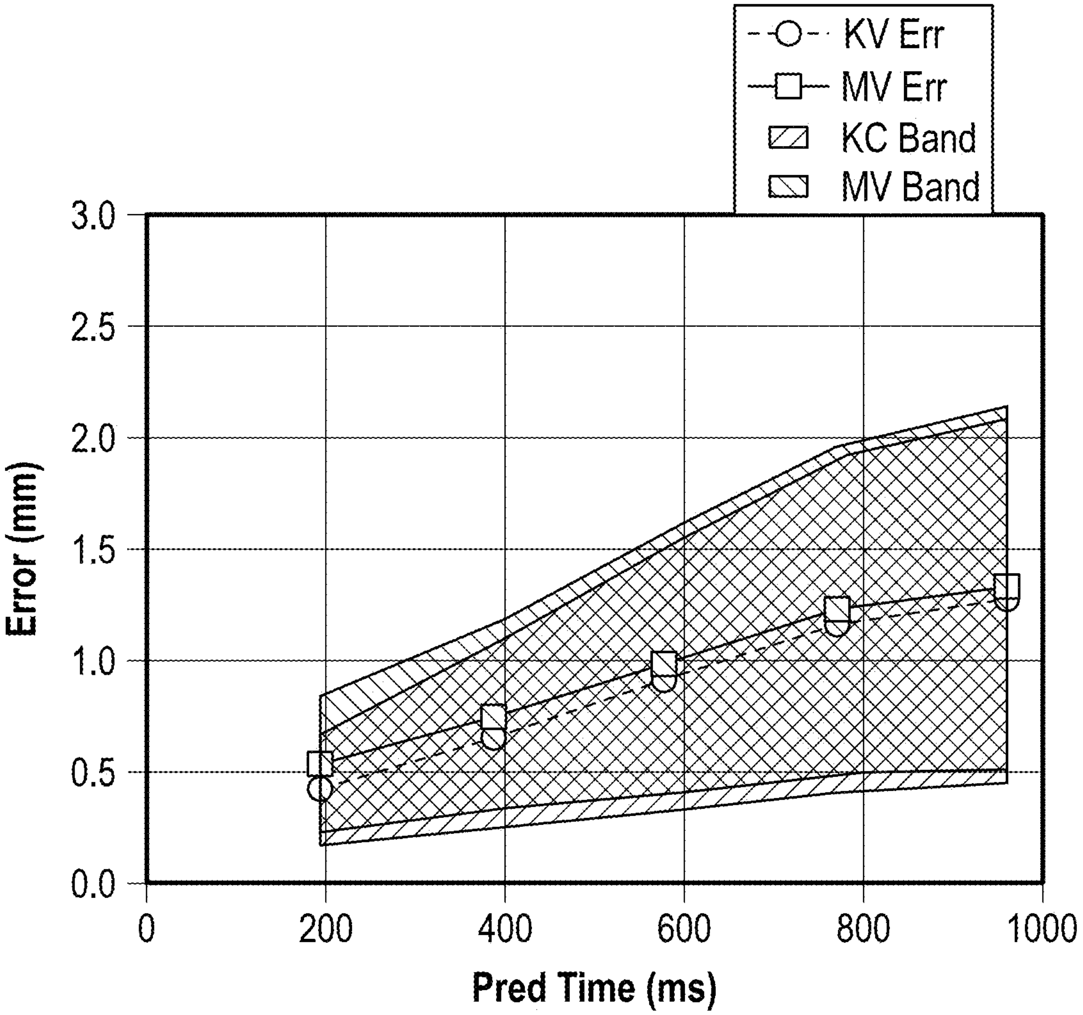
FIG. 5 illustrates a graph of the accuracy of the predicted trajectory with a simulated x-ray imager, according to an embodiment.

FIG. 5 shows a graph 500 of the accuracy of the predicted trajectory with a simulated x-ray imager. More specifically, the graph 500 of the accuracy of the predicted trajectory is illustrated with a simulated x-ray imager at sampling rate 5.2 Hz and gantry movement at 5 degree/sec. It can be observed that in average the error of the predicted trajectory is less than 1.0 mm for predicting signals within 500 ms and less than 1.5 mm within 1000 ms.

Figure 6:
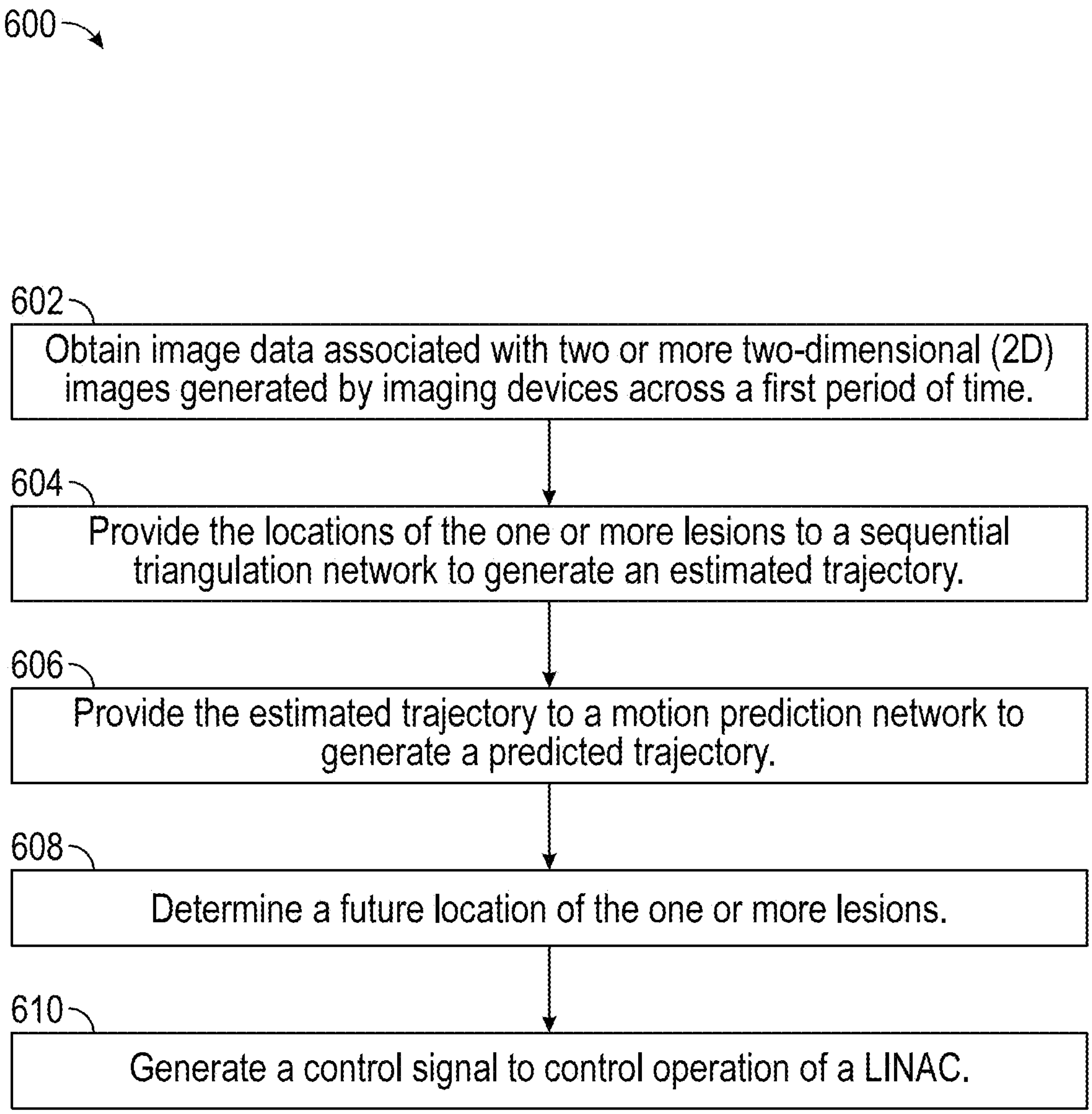
FIG. 6 illustrates a flow diagram of a process for predicting a location of a gross target volume in a patient during radiotherapy treatment, according to an embodiment.

FIG. 6 illustrates a flow diagram of a process for predicting a location of a gross target volume in a patient during radiotherapy treatment, according to an embodiment.

Referring to FIG. 6, illustrated is a flow diagram of a process 600 for predicting a location of a gross target volume in a patient during radiotherapy treatment, according to an embodiment. The process 600 includes operations 602-610. However, other embodiments can include additional or alternative operations or can omit one or more operations altogether. The process 600 is described as being executed by an analytics server, which can be the same as, or similar to, the analytics server 114*a* described in FIG. 1. However, one or more steps of the process 200 can be executed by any number of computing devices operating in the distributed computing system described in FIG. 1. For instance, one or more computing devices can locally perform part, or all of the operations described in FIG. 6.

At operation 602, the analytics server can obtain image data associated with two or more two-dimensional (2D) images generated by an imaging device. For example, the analytics server can obtain image data associated with two or more 2D images generated by a plurality of imaging devices positioned about a patient similar to as described above in process 200 of FIG. 2. The imaging devices can include X-ray machines and or the like. In some embodiments, the analytics server can obtain the image data from the plurality of imaging devices, where the plurality of imaging devices is positioned relative to a patient in a 3D space. In this example, the plurality of imaging devices can be positioned relative to the patient along with a medical device (e.g., that is the same as, or similar to, the medical device 160 of FIG. 1) such as a LINAC that is being moved to multiple control points established by a treatment plan to deliver energy to the patient. While the concepts of the present disclosure are discussed with respect to a LINAC, it will be understood that different types of medical devices (e.g., proton beam systems, etc.) are contemplated as being used instead of, or in addition to, the LINAC.

In one example, during RT treatment, the patient can be positioned in relation to a gantry of a LINAC that supports a magnetron or a klystron generating high-energy X-rays for delivery to the lesion of the patient as described herein. During treatment of the patient, the LINAC can be moved to a plurality of control points and configured to generate and transmit energy toward the patient at each control point. At each control point, the leaves of the LINAC's MLC can shape the X-rays so as to optimize energy delivery and conformance with the lesion of the patient, while minimizing the delivery of energy outside of the lesion (e.g., to one or more OARs). In some embodiments, a set of control points, MLC leaf configurations, and power levels at which energy is to be delivered can be established by a treatment plan generated prior to the procedure. As will be understood, the analytics server can be configured to perform operations to control the operation of the LINAC as described herein in accordance with a treatment plan developed for that patient.

In some embodiments, the analytics server can obtain the image data after generation of the image data during a first period of time. For example, the analytics server can obtain the image data at one or more points in time during the first period of time at or before when the patient is being treated. In this example, the imaging devices can be configured to generate images at a plurality of points in time during the period of time in which the patient is being observed (e.g., to condition one or more models as described herein to account for motion of one or more anatomical structures due to, for example, patient breathing, etc.) and/or treated. In some embodiments, the analytics server can obtain the image data from the one or more imaging devices, where the image data includes (e.g., represents) two or more X-ray images captured by the one or more imaging devices. The X-ray images can include 2D representations of at least a portion of the patient. For example, the X-ray images captured by the imaging devices can include corresponding 2D representations of at least a portion of the patient where the GTV being treated is located. To allow for the analytics server to obtain additional image data, the plurality of imaging devices can be configured to periodically and or continuously generate the image data and provide the image data to the analytics server during observation of the patient.

In some embodiments, the analytics server can determine the locations of one or more lesions represented by the image data at points in time across the first period of time (e.g., similar to as described above with respect to process 200). For example, the analytics server can compare the representations of the one or more events across the 2D images at points in time across the first period of time and determine the locations of the one or more lesions in response to this comparison. In some examples, the locations of the one or more lesions can be represented as 2D coordinates and/or 3D coordinates. Additionally, or alternatively, the locations of the one or more lesions can indicate a position and/or orientation (e.g., a pose) of the one or more lesions (and, by extension, a GTV associated with the one or more lesions). In examples, the analytics server can determine poses for each lesion of the one or more lesions at points in time across the first period of time based on the representation of the one or more lesions in the 2D images. As will be understood, the analytics server can determine the location of the one or more lesions, where the one or more lesions are located within the GTV of the patient similar to as described above with respect to process 200 of FIG. 2. Examples of techniques for determining the locations of the one or more lesions are also described in U.S. patent application Ser. No. 18/999,536 filed on Dec. 23, 2024, and Titled "systems and Methods for Determining a Location of a GROSS TARGET VOLUME OF A PATIENT," the contents of which are hereby incorporated by reference in their entirety and for all purposes.

At operation 604, the analytics server can provide the locations of the one or more lesions to a sequential triangulation network to generate an estimated trajectory. For example, the analytics server can provide the locations of the one or more lesions to a sequential triangulation network (e.g., a model such as a neural network, a deep neural network, a transformer or transformer-based network, etc., that is configured to perform one or more operations described herein to model one or more implicit functions) established by the two or more 2D images of the patient. The sequential triangulation network can then be configured to generate an output associated with (e.g., representing) an estimated trajectory based on the locations of the one or more lesions established by the two or more 2D images. The estimated trajectory can represent the observed motion of the one or more lesions in 3D space during the period of time that is determined based on the 2D images generated prior to or during RT treatment of the patient.

In some embodiments, the analytics server can cause the sequential triangulation network to generate the estimated trajectory for one or more lesions of the patient. For example, during RT treatment, the analytics server can capture two or more 2D images of one or more lesions of the patient. The analytics server can then provide the two or more 2D images as input to the sequential triangulation network to cause the sequential triangulation network to generate the output representing the estimated trajectory. The estimated trajectory can represent relative motion of the one or more lesions in the 3D space in which the patient is located.

The sequential triangulation network can be trained using a training dataset. For example, the analytics server can train the sequential triangulation network using a training dataset to generate the estimated trajectories of lesions of patients in response to obtaining (e.g., receiving, deriving, etc.) 2D images of the patient (e.g., X-ray images) and determining locations of the one or more lesions (e.g., established by the two or more 2D images captured during RT treatments). In examples, the analytics server can train the sequential triangulation network by providing the locations of the one or more lesions to cause the sequential triangulation network to generate respective outputs. In this example, the respective outputs can represent an estimated trajectory indicating the motion of the one or more lesions as observed across 2D images of the patients. The analytics server can then compare the outputs (e.g., the estimated trajectories to known trajectories established by the training dataset. The analytics server can then determine a difference between the estimated trajectories and the known trajectories (e.g., offsets between the estimated trajectories and the known trajectories), determine a loss based on the difference, and update one or more weights of the sequential triangulation network to reduce the loss upon subsequent execution of the sequential triangulation network by the analytics server. The analytics server can iteratively repeat this process until the sequential triangulation network converges (e.g., the model generates predictions that result in future locations with corresponding losses that satisfy a threshold value responding to an accepted accuracy for the sequential triangulation network).

In some embodiments, the known trajectories can be determined based on one or more four-dimensional CT (4DCT) scans. For example, the training dataset can be established based on 4DCT scans captured for one or more previously observed patients. In this example, the analytics server can generate a plurality of the 2D images at various gantry poses from the 4DCT scans of the previously observed patients and include the 2D images in the training dataset. The analytics server can similarly generate a plurality of trajectories from the 4DCT scans. In some embodiments, the analytics server can then train the sequential triangulation network as described above using the training data set established in accordance with the 4DCT scans.

In some embodiments, during RT treatment, the analytics server can condition the sequential triangulation network. For example, the analytics server can condition the sequential triangulation network based on locations of one or more lesions captured by imaging devices for a specific patient being treated. The analytics server can determine the locations of the one or more lesions based on the 2D images captured of the patient prior to, or during the RT treatment, and provide the locations to cause the sequential triangulation network to generate estimated trajectories. By providing the locations of the one or more lesions of the patient prior to or during treatment, the analytics server can train (e.g., update) this sequential triangulation network to model the motion of specific lesions within that patient. This can result in a more accurate determination of the location of the one or more lesions on a per patient basis.

At operation 606, the analytics server can provide the estimated trajectory to a motion prediction network to generate a predicted trajectory. For example, the analytics server can provide the estimated trajectory of the one or more lesions to a motion prediction network (e.g., a model such as a neural network, a deep neural network, a transformer or transformer-based network, etc., that is configured to perform one or more operations described herein to model one or more implicit functions) based on (e.g., in response to) generation of the estimated trajectory by the sequential triangulation network. The motion prediction network can be configured to generate an output associated with (e.g., representing) a predicted trajectory of expected motion of the one or more lesions within the 3D space where the patient is located over a second period of time. Specifically, the analytics server can cause the motion prediction network to generate the predicted trajectory for a period of time after the period of time represented by the estimated trajectory. The analytics server can then determine a location (e.g., a pose) of the one or more lesions using the predicted trajectory as described herein.

The motion prediction network can be trained using a training dataset. For example, the analytics server can train the motion prediction network using a training dataset to generate the predicted trajectories of lesions of patients in response to obtaining (e.g., receiving, deriving, etc.) an estimated trajectory of one or more lesions. In examples, the analytics server can train the motion prediction network by providing the locations of the one or more lesions of one or more patients represented in the training dataset at a point in time (e.g., corresponding to a final point in time represented by the estimated trajectory) and/or the estimated trajectory to cause the motion prediction network to generate respective outputs. In this example, the respective outputs can represent predicted trajectories representing expected motion of the one or more lesions of the respective patients within 3D spaces where the patients are located over a second period of time (after the period of time established by the estimated trajectory). The analytics server can then compare the outputs (e.g., the predicted trajectories) to known trajectories established by the training dataset. In response to this comparison, the analytics server can determine a difference between the predicted trajectories and the known trajectories (e.g., offsets between the predicted trajectories and the known trajectories), determine a loss based on the difference, and update one or more weights of the motion prediction network to reduce the loss upon subsequent execution of the motion prediction network by the analytics server. The analytics server can iteratively repeat this process until the motion prediction network converges (e.g., the model generates predictions that result in trajectories with corresponding losses that satisfy a threshold value responding to an accepted accuracy for the motion prediction network).

At operation 608, the analytics server can determine a future location of the one or more lesions. For example, the analytics server can determine a future location of the one or more lesions in response to the analytics server generating the predicted trajectory representing expected motion of the one or more lesions. In this example, the analytics server can determine the future location of the one or more lesions based on a location of the one or more lesions represented by the image data at the beginning of the second period of time and the predicted trajectory. In some embodiments, the analytics server can determine the future location (e.g., the future pose) up to one or more lesions based on the analytics server applying a transformation to the location of the one or more lesions at the beginning of the second period of time in accordance with the predicted trajectory. It will be understood, the analytics server and then iteratively repeat one or more of operations 602-606 and predict future locations of the one or more lesions within the 3D space during the course of the RT treatment.

At operation 610, the analytics server can generate a control signal to cause a medical device to move from a current position to a future pose. For example, the analytics server can determine a pose of the medical device at the first point in time (at the beginning of the second period of time as described above). At that first point in time, the analytics server can configure the medical device to generate and transmit energy towards the GTV of the patient based on the relative position of the patient compared to the 3D space in which the patient is located and/or the relative position of the medical device. In this example, the analytics server can cause the medical device to generate and transmit the energy in accordance with the treatment plan similar to as described by process 200. In some embodiments, the analytics server can then predict future locations of the GTV during the course of the RT treatment as described above. For example, the analytics server can predict future locations of the GTV as the medical device is moved from control point to control point and activated to deliver energy to the GTV of the patient. The analytics server can then compare the predicted future locations to the locations established by the treatment plan and control operation of the medical device such that the medical device targets the GTV at the (predicted) future location.

In some embodiments, the analytics server can determine a beam-eye view. For example, the analytics server can determine a beam-eye view representing a view of the GTV relative to one or more components of the medical device (e.g., a collimator of a LINAC). The beam-eye view can be represented as a 2D representation of the GTV from the point of view of the one or more components of the LINAC. In some embodiments, the beam-eye view can be used by the analytics server when targeting the GTV using the medical device during performance of the RT treatment plan.

Figure 7:
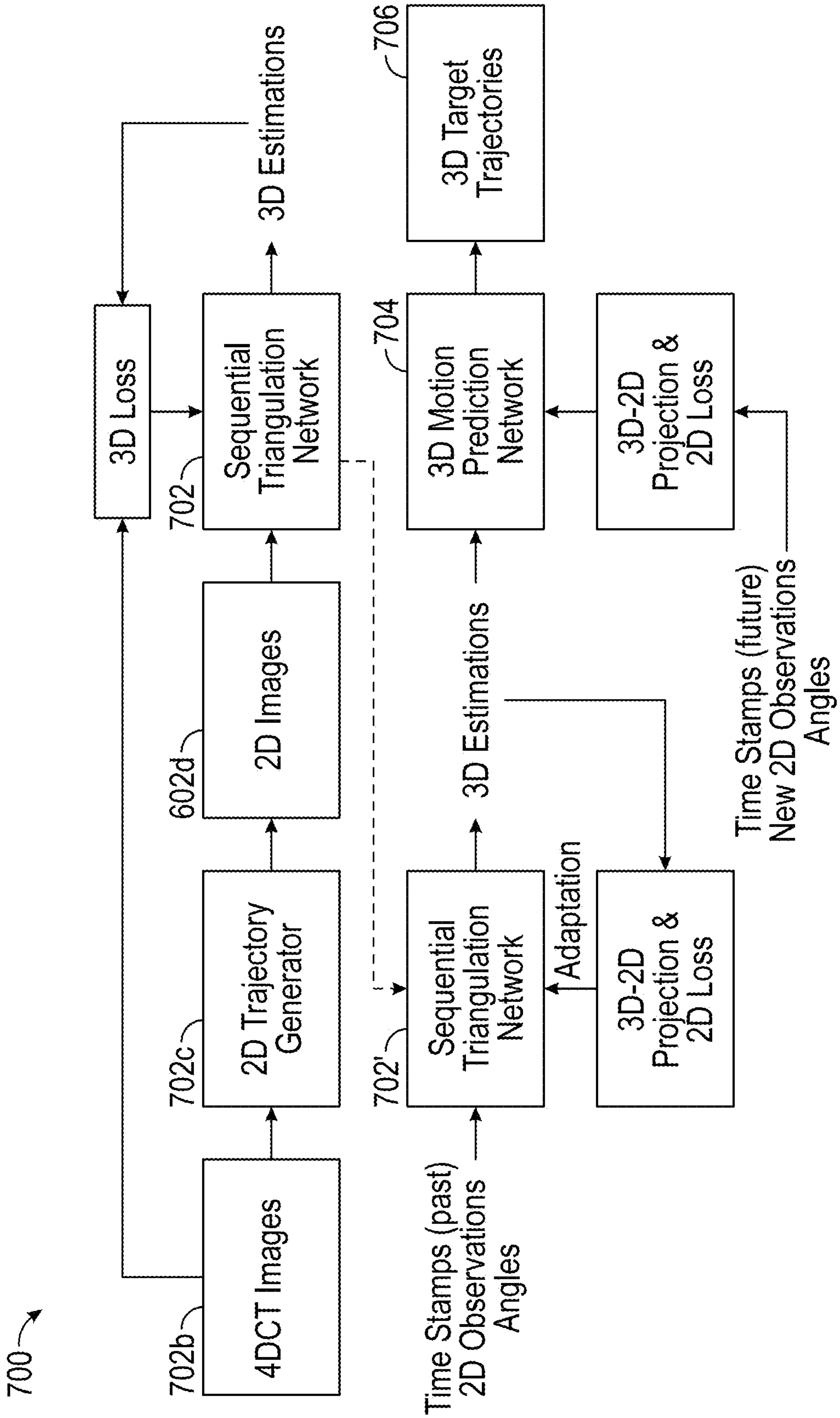
FIG. 7 illustrates an example implementation of a process for predicting a location of a gross target volume in a patient during radiotherapy treatment, according to an embodiment.

FIG. 7 illustrates an example implementation 700 of a process for predicting a location of a gross target volume in a patient during radiotherapy treatment, according to an embodiment. As shown in FIG. 7, the implementation 700 involves execution of a sequential triangulation network 702 and a motion prediction network 704. In some examples, the sequential triangulation network 702 and/or the motion prediction network 704 can be the same as, or similar to, the models described above with respect to FIG. 6. In some embodiments, one or more of the operations described with respect to the implementation 700 can be executed by an analytics server that is the same as, or similar to, the analytics server 114*a* of FIG. 1 and/or the analytics server discussed with respect to FIG. 2.

In some embodiments, the implementation 700 can include generating multiple 2D projected trajectories using the 2D trajectory generator 702*c*. For example, one or more 4DCT images 702*b* can be obtained and used to determine (e.g., derive) 3D trajectories. The 2D trajectory generator 702*c* can then determine various angles and time stamps from the 3D trajectories to establish a training dataset and allow for training of the sequential triangulation network 702 similar to as described above to configure the sequential triangulation network 702 to reconstruct 3D trajectories (referred to as estimated trajectories) from sequential 2D X-ray images (also referred to as 2D observations) from different angles during a first period of time.

The trained sequential triangulation network 702' can be further updated for a specific patient based on 2D images generated by imaging device directed toward the patient during RT treatment. The estimated trajectories can be provided as input to a motion prediction network 704 to predict 3D trajectory in the future timeframe. Both the sequential triangulation network 702' and motion prediction network 704 can be modeled with implicit functions as described herein. In some embodiments, external surrogate signals may be optionally used as an input to one or more of the sequential triangulation networks 702, 702' or motion prediction network 704.

Figure 8:
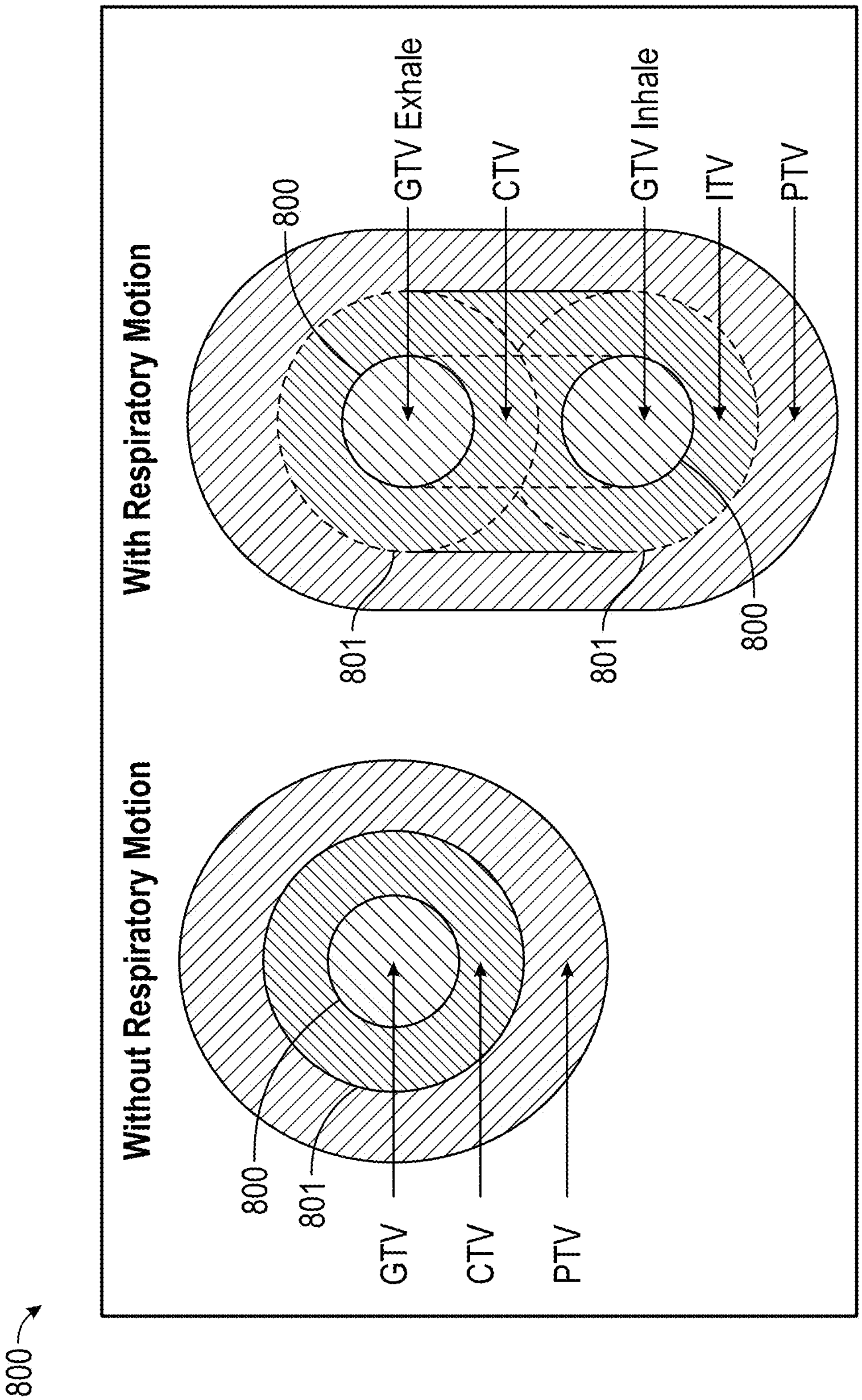
FIG. 8 illustrates an example of motion by a gross target volume as a result of respiration, according to an embodiment.

FIG. 8 illustrates an example of motion by a gross target volume (GTV) 800 as a result of respiration, according to an embodiment. In some embodiments, the GTV 800 can be the same as, or similar to, the GTV described above. In a first state 800*a*, the GTV 800 can remain stationary; and during respiration 800*b* the GTV 800 can move from a first location to a second location. As illustrated, when the GTV 800 is moving or not moving, the GTV can be surrounded at least in part by a clinical target volume (CTV). The CTV can similarly be surrounded at least in part by a planning target volume (PTV).

When moving (e.g., from a first location to a second location during respiration by an individual) the GTV 800 and CTV 801 can move in coordination with the PTV. For example, during respiration, the GTV 800, which represents one or more lesions, can shift significantly due to the movement of surrounding tissues and organs. This movement, particularly in relation to the PTV, can be modeled using the techniques described herein. In examples, the CTV 801 encompasses not only the GTV 800 but also any subclinical disease that may be present, while the internal target volume (ITV) addresses uncertainties due to organ motion based on CTV, and PTV can include additional margins to account for uncertainties in treatment delivery, such as patient positioning and setup errors. As shown in 800*b*, during an exhale, the GTV 800 and CTV 801 can move upward relative to the ITV and PTV; and during an inhale, the GTV 800 and CTV 801 can move downward relative to the ITV and PTV. It will be understood that, while motion is illustrated in one dimension, the GTV 800 can move in a variety of directions within three-dimensional space.

The presently-disclosed techniques will be better understood with reference to the following enumerated examples:

1. A system for predicting a location of a gross target volume in a patient during radiotherapy treatment by modeling motion of one or more lesions of the gross target volume over time, the system comprising: one or more processors configured to: obtain image data associated with a plurality of two-dimensional (2D) images, the image data generated by one or more imaging devices positioned about a patient and representing locations of one or more lesions across a first period of time; provide the locations of the one or more lesions to a sequential triangulation network to cause the sequential triangulation network to generate an estimated trajectory representing motion of the one or more lesions over the first period of time; provide the estimated trajectory to a motion prediction network to cause the motion prediction network to generate a predicted trajectory representing expected motion of the one or more lesions within a three-dimensional (3D) space over a second period of time; determine a future location of the one or more lesions based on a location of the one or more lesions and the predicted trajectory; and generate a control signal to cause a linear accelerator (LINAC) to move from a first pose to a second pose to adjust a beam path of the linear accelerator based on the future location of the one or more lesions.
2. The system of any of the previous examples, further comprising: determining the locations of the one or more lesions across the first period of time based on the plurality of 2D images.
3. The system of any of the previous examples, wherein the one or more processors to provide the image data to the sequential triangulation network are configured to: provide the image data to the sequential triangulation network, where the sequential triangulation network is trained based on a plurality of four-dimensional computed tomography (CT) scans corresponding to a plurality of previously-observed patients.
4. The system of any of the previous examples, wherein the sequential triangulation network is trained based on a plurality of estimated 2D images extracted from four-dimensional CT scans generated for the one or more patients.
5. The system of any of the previous examples, wherein the one or more processors configured to provide the locations of the one or more lesions to a sequential triangulation network are configured to: condition the sequential triangulation network based on at least a portion of the locations of the one or more lesions.
6. The system of any of the previous examples, wherein the plurality of 2D images comprise a plurality of X-ray images, and wherein the one or more processors configured to obtain the image data are configured to: obtain a plurality of X-ray images from the one or more imaging devices, the plurality of X-ray images comprising two-dimensional (2D) representations of at least a portion of the patient across the first period of time.

7. The system of any of the previous examples, wherein the location of the one or more lesions across the first period of time represent poses of the one or more lesions in the 3D space.

8. The system of any of the previous examples, wherein the one or more processors are further configured to: determine a beam-eye view (BEV) of the one or more lesions based on the future location of the one or more lesions and a pose of the LINAC at a second point in time.

9. A method for predicting a location of a gross target volume in a patient during radiotherapy treatment by modeling motion of one or more lesions of the gross target volume over time, the method comprising: obtaining, by one or more processors, image data associated with a plurality of two-dimensional (2D) images, the image data generated by one or more imaging devices positioned about a patient and representing locations of one or more lesions across a first period of time; providing, by the one or more processors, the locations of the one or more lesions to a sequential triangulation network to cause the sequential triangulation network to generate an estimated trajectory representing motion of the one or more lesions over the first period of time; providing, by the one or more processors, the estimated trajectory to a motion prediction network to cause the motion prediction network to generate a predicted trajectory representing expected motion of the one or more lesions within a three-dimensional (3D) space over a second period of time; determining, by the one or more processors, a future location of the one or more lesions based on a location of the one or more lesions and the predicted trajectory; and generating, by the one or more processors, a control signal to cause a linear accelerator (LINAC) to move from a first pose to a second pose to adjust a beam path of the linear accelerator based on the future location of the one or more lesions.

10. The method of any of the previous examples, further comprising: determining, by the one or more processors, the locations of the one or more lesions across the first period of time based on the plurality of 2D images.

11. The method of any of the previous examples, wherein providing the image data to the sequential triangulation network comprises: providing, by the one or more processors, the image data to the sequential triangulation network, where the sequential triangulation network is trained based on a plurality of four-dimensional computed tomography (CT) scans corresponding to a plurality of previously-observed patients.

12. The method of any of the previous examples, wherein the sequential triangulation network is trained based on a plurality of estimated 2D images extracted from four-dimensional CT scans generated for the one or more patients.

13. The method of any of the previous examples, wherein providing the locations of the one or more lesions to a sequential triangulation network comprises: conditioning, by the one or more processors, the sequential triangulation network based on at least a portion of the locations of the one or more lesions.

14. The method of any of the previous examples, wherein the plurality of 2D images comprise one or more X-ray images, and wherein obtaining the image data comprises: obtaining, by the one or more processors, a plurality of X-ray images from the plurality of imaging devices, the plurality of X-ray images comprising two-dimensional (2D) representations of at least a portion of the patient across the first period of time.

15. The method of any of the previous examples, wherein the location of the one or more lesions across the first period of time represent poses of the one or more lesions in the 3D space.

16. The method of any of the previous examples, further comprising: determining, by the one or more processors, a beam-eye view (BEV) of the one or more lesions based on the future location of the one or more lesions and a pose of the LINAC at a second point in time.

17. A computer program storing instructions thereon that, when executed by one or more processors, cause the one or more processors to perform the steps of: obtain image data associated with a plurality of two-dimensional (2D) images, the image data generated by one or more imaging devices positioned about a patient and representing locations of one or more lesions across a first period of time; provide the locations of the one or more lesions to a sequential triangulation network to cause the sequential triangulation network to generate an estimated trajectory representing motion of the one or more lesions over the first period of time; provide the estimated trajectory to a motion prediction network to cause the motion prediction network to generate a predicted trajectory representing expected motion of the one or more lesions within a three-dimensional (3D) space over a second period of time; determine a future location of the one or more lesions based on a location of the one or more lesions and the predicted trajectory; and generate a control signal to cause a linear accelerator (LINAC) to move from a first pose to a second pose to adjust a beam path of the linear accelerator based on the future location of the one or more lesions.

18. The computer program of any of the previous examples, wherein the instructions further cause the one or more processors to perform the steps of: determining the locations of the one or more lesions across the first period of time based on the plurality of 2D images.

19. The computer program of any of the previous examples, wherein the instructions that cause the one or more processors to provide the image data to the sequential triangulation network cause the one or more processors to perform the steps of: providing the image data to the sequential triangulation network, where the sequential triangulation network is trained based on a plurality of four-dimensional computed tomography (CT) scans corresponding to a plurality of previously-observed patients.

20. The computer program of any of the previous examples, wherein the sequential triangulation network is trained based on a plurality of estimated 2D images extracted from four-dimensional CT scans generated for the one or more patients.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of this disclosure or the claims.

Embodiments implemented in computer software (e.g., computer programs, computer program products, etc.) can be implemented in software, firmware, middleware, microcode, hardware description languages, or any combination thereof. A code segment or machine-executable instructions can represent a procedure, a function, a subprogram, a program, a routine, a subroutine, a module, a software package, a class, or any combination of instructions, data structures, or program statements. A code segment can be coupled to another code segment or a hardware circuit by passing or receiving information, data, arguments, parameters, or memory contents. Information, arguments, parameters, data, etc., can be passed, forwarded, or transmitted via any suitable means, including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions can be stored as one or more instructions or code on a non-transitory computer-readable or processor-readable storage medium. The steps of a method or algorithm disclosed herein can be embodied in a processor-executable software module, which can reside on a computer-readable or processor-readable storage medium. A non-transitory computer-readable or processor-readable media includes both computer storage media and tangible storage media that facilitate the transfer of a computer program from one place to another. A non-transitory processor-readable storage media can be any available media that can be accessed by a computer. By way of example, and not limitation, such non-transitory processor-readable media can comprise RAM, ROM, EEPROM, CD-ROM or other optical disk storage, magnetic disk storage or other magnetic storage devices, or any other tangible storage medium that can be used to store desired program code in the form of instructions or data structures and that can be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm can reside as one or any combination or set of codes or instructions on a non-transitory processor-readable medium or computer-readable medium, which can be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein can be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A system for predicting a location of a gross target volume in a patient during radiotherapy treatment by modeling motion of one or more lesions of the gross target volume over time, the system comprising:
- one or more processors configured to:
  - obtain image data associated with a plurality of two-dimensional (2D) images, the image data generated by one or more imaging devices positioned about a patient and representing locations of one or more lesions across a first period of time;
  - provide the locations of the one or more lesions to a sequential triangulation network to cause the sequential triangulation network to generate an estimated trajectory representing motion of the one or more lesions over the first period of time;
  - provide the estimated trajectory to a motion prediction network to cause the motion prediction network to generate a predicted trajectory representing expected motion of the one or more lesions within a three-dimensional (3D) space over a second period of time;
  - determine a future location of the one or more lesions based on a location of the one or more lesions and the predicted trajectory; and
  - generate a control signal to cause a linear accelerator (LINAC) to move from a first pose to a second pose to adjust a beam path of the linear accelerator based on the future location of the one or more lesions.

2. The system of claim 1, further comprising:
- determining the locations of the one or more lesions across the first period of time based on the plurality of 2D images.

3. The system of claim 1, wherein the one or more processors to provide the image data to the sequential triangulation network are configured to:
- provide the image data to the sequential triangulation network, where the sequential triangulation network is trained based on a plurality of four-dimensional computed tomography (CT) scans corresponding to a plurality of previously-observed patients.

4. The system of claim 3, wherein the sequential triangulation network is trained based on a plurality of estimated 2D images extracted from four-dimensional CT scans generated for the one or more patients.

5. The system of claim 1, wherein the one or more processors configured to provide the locations of the one or more lesions to a sequential triangulation network are configured to:
- condition the sequential triangulation network based on at least a portion of the locations of the one or more lesions.

6. The system of claim 1, wherein the plurality of 2D images comprise a plurality of X-ray images, and wherein the one or more processors configured to obtain the image data are configured to:

obtain a plurality of X-ray images from the one or more imaging devices, the plurality of X-ray images comprising two-dimensional (2D) representations of at least a portion of the patient across the first period of time.

7. The system of claim 1, wherein the location of the one or more lesions across the first period of time represent poses of the one or more lesions in the 3D space.

8. The system of claim 1, wherein the one or more processors are further configured to:

determine a beam-eye view (BEV) of the one or more lesions based on the future location of the one or more lesions and a pose of the LINAC at a second point in time.

9. A method for predicting a location of a gross target volume in a patient during radiotherapy treatment by modeling motion of one or more lesions of the gross target volume over time, the method comprising:

obtaining, by one or more processors, image data associated with a plurality of two-dimensional (2D) images, the image data generated by one or more imaging devices positioned about a patient and representing locations of one or more lesions across a first period of time;

providing, by the one or more processors, the locations of the one or more lesions to a sequential triangulation network to cause the sequential triangulation network to generate an estimated trajectory representing motion of the one or more lesions over the first period of time;

providing, by the one or more processors, the estimated trajectory to a motion prediction network to cause the motion prediction network to generate a predicted trajectory representing expected motion of the one or more lesions within a three-dimensional (3D) space over a second period of time;

determining, by the one or more processors, a future location of the one or more lesions based on a location of the one or more lesions and the predicted trajectory; and generating, by the one or more processors, a control signal to cause a linear accelerator (LINAC) to move from a first pose to a second pose to adjust a beam path of the linear accelerator based on the future location of the one or more lesions.

10. The method of claim 9, further comprising:

determining, by the one or more processors, the locations of the one or more lesions across the first period of time based on the plurality of 2D images.

11. The method of claim 9, wherein providing the image data to the sequential triangulation network comprises:

providing, by the one or more processors, the image data to the sequential triangulation network, where the sequential triangulation network is trained based on a plurality of four-dimensional computed tomography (CT) scans corresponding to a plurality of previously-observed patients.

12. The method of claim 11, wherein the sequential triangulation network is trained based on a plurality of estimated 2D images extracted from four-dimensional CT scans generated for the one or more patients.

13. The method of claim 9, wherein providing the locations of the one or more lesions to a sequential triangulation network comprises:

conditioning, by the one or more processors, the sequential triangulation network based on at least a portion of the locations of the one or more lesions.

14. The method of claim 9, wherein the plurality of 2D images comprise one or more X-ray images, and wherein obtaining the image data comprises:

obtaining, by the one or more processors, a plurality of X-ray images from the plurality of imaging devices, the plurality of X-ray images comprising two-dimensional (2D) representations of at least a portion of the patient across the first period of time.

15. The method of claim 9, wherein the location of the one or more lesions across the first period of time represent poses of the one or more lesions in the 3D space.

16. The method of claim 9, further comprising:

determining, by the one or more processors, a beam-eye view (BEV) of the one or more lesions based on the future location of the one or more lesions and a pose of the LINAC at a second point in time.

17. A non-transitory computer-readable medium storing instructions thereon that, when executed by one or more processors, cause the one or more processors to:

obtain image data associated with a plurality of two-dimensional (2D) images, the image data generated by one or more imaging devices positioned about a patient and representing locations of one or more lesions across a first period of time;

provide the locations of the one or more lesions to a sequential triangulation network to cause the sequential triangulation network to generate an estimated trajectory representing motion of the one or more lesions over the first period of time;

provide the estimated trajectory to a motion prediction network to cause the motion prediction network to generate a predicted trajectory representing expected motion of the one or more lesions within a three-dimensional (3D) space over a second period of time;

determine a future location of the one or more lesions based on a location of the one or more lesions and the predicted trajectory; and generate a control signal to cause a linear accelerator (LINAC) to move from a first pose to a second pose to adjust a beam path of the linear accelerator based on the future location of the one or more lesions.

18. The non-transitory computer-readable medium of claim 17, wherein the instructions further cause the one or more processors to:

determine the locations of the one or more lesions across the first period of time based on the plurality of 2D images.

19. The non-transitory computer-readable medium of claim 17, wherein the instructions that cause the one or more processors to provide the image data to the sequential triangulation network cause the one or more processors to:

provide the image data to the sequential triangulation network, where the sequential triangulation network is trained based on a plurality of four-dimensional computed tomography (CT) scans corresponding to a plurality of previously-observed patients.

20. The non-transitory computer-readable medium of claim 19, wherein the sequential triangulation network is trained based on a plurality of estimated 2D images extracted from four-dimensional CT scans generated for the one or more patients.

* * * * *